United States Patent
LeBoeuf

(10) Patent No.: US 6,388,035 B1
(45) Date of Patent: May 14, 2002

(54) HYDROPHOBICALLY-BOUND, HYDROPHILIC COATING COMPOSITIONS FOR SURGICAL IMPLANTS

(75) Inventor: Albert R. LeBoeuf, Burleson, TX (US)

(73) Assignee: Alcon Universal Ltd., Hunenberg (SE)

( * ) Notice: Subject to any disclaimer, the term of this patent is extended or adjusted under 35 U.S.C. 154(b) by 125 days.

(21) Appl. No.: 09/645,274

(22) Filed: Aug. 24, 2000

Related U.S. Application Data
(60) Provisional application No. 60/152,169, filed on Sep. 2, 1999.

(51) Int. Cl.$^7$ .................................................. C08F 26/08
(52) U.S. Cl. ...................... 526/264; 526/258; 526/263; 526/328; 526/328.5
(58) Field of Search ................................ 526/258, 263, 526/264, 328, 328.5

(56) References Cited

U.S. PATENT DOCUMENTS

| | | | |
|---|---|---|---|
| 4,578,504 A | 3/1986 | Hammar | 560/112 |
| 4,638,040 A | 1/1987 | Hammar | 526/245 |
| 4,673,539 A | 6/1987 | Hammar et al. | 264/1.1 |
| 4,786,446 A | 11/1988 | Hammar et al. | 264/2.6 |
| 4,921,884 A | 5/1990 | Hammar et al. | 523/106 |
| 4,931,519 A | 6/1990 | Song et al. | 56/258 |
| 5,002,792 A | 3/1991 | Vegoe | 427/2 |
| 5,094,876 A | 3/1992 | Goldberg et al. | 427/2 |
| 5,108,776 A | 4/1992 | Goldberg et al. | 427/2 |
| 5,130,160 A | 7/1992 | Goldberg et al. | 427/2 |
| 5,152,787 A | 10/1992 | Hamblen | 623/6 |
| 5,290,548 A | 3/1994 | Goldberg et al. | 424/78.18 |
| 5,290,892 A | 3/1994 | Namdaran et al. | 526/259 |
| 5,403,901 A | 4/1995 | Namdaran et al. | 526/259 |
| 5,554,187 A | 9/1996 | Rizzo, III | 623/6 |
| 5,603,774 A | 2/1997 | LeBoeuf et al. | 134/1 |
| 5,888,243 A | 3/1999 | Silverstrini | 623/5 |

FOREIGN PATENT DOCUMENTS

| | | |
|---|---|---|
| EP | 0 559 820 B1 | 2/1998 |
| EP | 0 908 476 A2 | 4/1999 |
| JP | 11056999 A | 3/1999 |
| WO | WO 95/11279 | 4/1995 |
| WO | WO 96/40303 | 12/1996 |
| WO | WO 99/08136 | 2/1999 |
| WO | 99/11303 A1 | 3/1999 |
| WO | WO 99/52570 | 10/1999 |
| WO | 00/34804 | 6/2000 |

OTHER PUBLICATIONS

Brook, "Thermoplastic Hydrogels," *British Polymer Journal*, vol. 23, pp. 257–259 (1990).

Capozza et al., "Advanced in Thermoplastic Hydrogels," *Polymer Preprints*, vol. 31(2), p. 57 (1990).

Carbutt, "A Novel Thermoplastic Hydrogel," Master Thesis submitted at University of Lowell (1983).

Liu et al., "Preparation and Characterization of Some Linear Copolymers as Precursors to Thermoplastic Hydrogels," *Eur. Polym. J.*, vol. 30(4), pp. 457–463 (1994).

Regulski et al., "Isocyanatoethyl Methacrylate II: The Blocked Isocyanate Derivatives, Preparation and Deblocking," *ACS Organic Coatings & Applied Polymer Science Proceedings*, vol. 48, p. 998 (1983).

Regulski et al., "Isocyantoethyl Methacrylate III: Polymerization, Formulation and Evaluation of Blocked IEM Derivatives," *ACS Organic Coatings & Applied Polymer Science Proceedings*, vol. 48, pp. 1003–1007 (1983).

*Primary Examiner*—Helen L. Pezzuto
(74) *Attorney, Agent, or Firm*—Patrick M. Ryan

(57) ABSTRACT

Hydrophilic coatings for implants are disclosed. The coatings are hydrophobically bound to the implant, but are not covalently cross-linked or covalently anchored to the implant's surface.

9 Claims, No Drawings

HYDROPHOBICALLY-BOUND, HYDROPHILIC COATING COMPOSITIONS FOR SURGICAL IMPLANTS

This application claims priority from U.S. Provisional application, U.S. Serial No. 60/152,169, filed Sep. 2, 1999.

FIELD OF THE INVENTION

This invention relates to coatings for surgical implants. In particular, the present invention relates to hydrophilic copolymers that are hydrophobically bound to the surface of surgical implants.

BACKGROUND OF THE INVENTION

Both rigid and foldable implantable ophthalmic lens materials are known. The most common rigid material used in ophthalmic implants is polymethyl methacrylate ("PMMA"). Foldable intraocular lens ("IOL") materials can generally be divided into three categories: silicone materials, hydrogel materials, and non-hydrogel ("hydrophobic") acrylic materials. See, for example, *Foldable Intraocular Lenses*, Ed. Martin et al., Slack Incorporated, Thorofare, N.J. (1993). For purposes of the present application, hydrophobic acrylic materials are acrylic materials that absorb less than approximately 5% water at room temperature.

Silicone and non-hydrogel acrylic materials used in ophthalmic implants can damage endothelial cells and perhaps other cells or tissues as well during or after the implant's insertion in the eye. These materials are generally hydrophobic and/or tacky and can pull cells off of eye tissues that contact the implant. Particularly in the case of phakic IOL's implanted between the capsular bag and the iris, there is significant potential for physical contact between the implant and surrounding cells or tissue even after the implant reaches its target location.

SUMMARY OF THE INVENTION

The present invention relates to hydrophilic coating compositions for surgical implants, particularly ophthalmic implants comprising silicone or non-hydrogel acrylic materials. More specifically, the present invention relates to a coating material for an implant where the coating material comprises a copolymer of 2-phenylethyl (meth)acrylate and N-vinyl pyrrolidone ("NVP"). The coating material is capable of absorbing from about 40 to about 90% water. Despite its relatively high water content, the coating material of the present invention is sufficiently tough to withstand folding or handling with forceps without rupturing.

The present invention also relates to a method for applying a coating comprising a copolymer of 2-phenylethyl (meth)acrylate and NVP to an implant's surface, wherein the copolymer lacks a cross-linking monomer. The method comprises dissolving the copolymer in a solvent to form a coating solution, contacting the coating solution with the implant's surface, and drying the coated implant.

DETAILED DESCRIPTION OF THE INVENTION

Unless indicated otherwise, all amounts are expressed as weight %.

The coating material of the present invention is a copolymer of 2-phenylethyl (meth)acrylate and NVP. The coating material is attached to the substrate by means of hydrophobic or "physical" (i.e., non-covalent) cross-linking. The coating material is also internally cross-linked by non-covalent cross-linking. The coating material is capable of absorbing from about 40 to about 90% water, preferably from about 65 to about 75% water. The proportion of the copolymer's monomers will depend on the desired water content, with individual concentrations generally ranging from about 25 to about 60% for 2-phenylethyl (meth) acrylate and about 40 to about 75% for NVP. Copolymers of 2-phenylethyl methacrylate ("2-PEMA") and NVP are preferred. In the preferred case where the desired water content is about 65–75%, the copolymeric coating material comprises from about 35 to about 45% 2-PEMA and from about 40 to about 50% NVP.

The copolymeric coating material is prepared by combining the 2-phenylethyl (meth)acrylate and NVP ingredients with a polymerization initiator (generally about 2% or less) to form a coating composition and curing the coating composition. Any type of polymerization initiator may be used, including thermal initiators and photoinitiators. A preferred initiator is the benzoylphosphine oxide initiator, 2,4,6-trimethyl-benzoyldiphenylophosphine oxide ("TPO"), which is activated by blue-light. Suitable thermal initiators include the conventional peroxides t-butyl peroctoate and bis-azoisobutronitrile. Suitable UV initiators include benzoin methyl ether and Darocur 1173.

In addition to the 2-phenylethyl (meth)acrylate, NVP, and polymerization initiator, the coating copolymers optionally include one or more ingredients selected from the group consisting of UV absorbers that are copolymerizable with the 2-phenylethyl (meth)acrylate and NVP ingredients; blue-light blocking colorants that are copolymerizable with the 2-phenylethyl (meth)acrylate and NVP ingredients; reactive plasticizers to minimize haze or crazing; and chain transfer agents to minimize cross-linking within the coating copolymer.

Ultraviolet absorbing chromophores can be any compound which absorbs light having a wavelength shorter than about 400 nm, but does not absorb any substantial amount of visible light. Suitable copolymerizable ultraviolet absorbing compounds are the substituted 2-hydroxybenzophenones disclosed in U.S. Pat. No. 4,304,895 and the 2-hydroxy-5-acryloxyphenyl -2H-benzotriazoles disclosed in U.S. Pat. No. 4,528,311. The most preferred ultraviolet absorbing compound is 2-(3'-methallyl-2'-hydroxy-5'-methyl phenyl) benzotriazole. Suitable polymerizable blue-light blocking chromophores include those disclosed in U.S. Pat. No. 5,470,932. If a blue-light activated polymerization initiator is chosen and a blue-light blocking colorant is added, the polymerization initiator identity or concentration may have to be adjusted to minimize any interference.

Suitable reactive plasticizers or softening agents include polyethylene glycol (200–2000) mono(meth)acrylates and polyethylene glycol (200–2000) monomethylether mono (meth)acrylates. Methacrylates are preferred, with PEG (400)monomethylether monomethacrylate most preferred. If needed or desired, the amount of the reactive plasticizer will range from about 5 to about 25%. Depending on the implant's function and the thickness of the coating, some degree of haze or crazing may be tolerated such that a reactive plasticizer may not be required.

The chain transfer agent, if present, is typically added in an amount ranging from 0.01 to 0.4%. Many chain transfer agents are known in the art. Examples of suitable chain transfer agents include 1-dodecanethiol and 2-mercaptoethanol.

After the coating copolymer is cured, it is purified by extraction to remove water-soluble components and low-molecular weight hydrophobic components. This can be accomplished by a two-stage extraction where the first stage is an aqueous extraction and the second is a non-aqueous extraction. The resulting coating copolymer is extracted in water, typically for 12–20 hours to remove aqueous extractables, such as N-vinyl pyrrolidone or low-molecular weight polyvinyl pyrrolidone. After the coating copolymer is extracted in water, it is dissolved in an organic solvent, such as methylene chloride. The resulting solution containing the dissolved polymer is added to a bath of volatile aliphatic solvent(s), such as heptane or hexane, to precipitate the coating copolymer. The precipitated coating copolymer is collected by, for example, filtration using a scintered glass filter and then dried, preferably under vacuum at room temperature.

After the coating copolymer is purified, a coating solution is prepared by dissolving the coating copolymer in a solvent or mixture of solvents, such as a 50:50 (parts by weight) mixture of ethanol and 2-pentanone. The solvent or mixture of solvents is preferably chosen to give a clear, homogenous coating solution where the chosen solvent or solvent mixture does not evaporate so quickly that it leaves a hazy coating.

The concentration of the coating copolymer in the coating solution will depend on the desired coating thickness. Other factors that will influence the thickness of the coating include the viscosity of the coating solution, the temperature of the coating solution and the implant, and the evaporation rate of the chosen solvent(s). In general, the coatings of the present invention will be no more than 1 $\mu$m thick, and preferably will be about 0.5 $\mu$m thick. A minimum coating thickness of about 0.01 $\mu$m is likely necessary to allow the coating to survive any manipulation of the implant (such as the folding of an IOL) and any abrasion caused during implantation or extended residence at the target site in a patient. A concentration of coating copolymer of about 4–5% in the coating solution will typically produce a coating about 0.5 $\mu$m thick in a dip-coating process.

The coating solution is applied to the implant by conventional techniques, such as spin- or dip-coating processes. Dip-coating is preferred. The implant is preferably dipped quickly so as to minimize any swelling of the implant caused by the solvent in the coating solution.

After the coating is applied to the implant, the coating is dried. A two-stage drying process is preferred. First, the coated implant is allowed to dry in air until most or all of the solvent has evaporated (generally $\leq$15 minutes). Second, the coated implant is baked at elevated temperature, about 40–100° C., to eliminate as much of the remaining solvent as possible. A preferred drying process involves room temperature air drying for 15 minutes, followed by baking at 70° C. for about 30 minutes.

The coating can be easily removed by a variety of organic solvents or solvent mixtures, including the same solvent used as the base in the preparation of the coating solution. The coating cannot be removed by water, however.

Before the coated implant is manipulated, the coating is preferably hydrated for several seconds to minimize crazing or other damage to the coating.

The implants suitable for coating with the hydrophilic coatings of the present invention are preferably made of hydrophobic acrylic materials, but could also be constructed of silicone or silicone-acrylic copolymers. Preferred hydrophobic acrylic materials are those polymeric materials described in U.S. Pat. Nos. 5,290,892 and 5,693,095, the entire contents of which are hereby incorporated by reference. In the case where the implant is an IOL, the coatings of the present invention may be used in conjunction with substrate materials intended for use as a "hard" IOL (that is inserted in an unfolded state) or a "foldable" or "soft" IOL (that is inserted in a folded or compressed state). Suitable IOL materials to be coated include those disclosed in U.S. Pat. Nos. 5,693,095 or 5,331,073. The coating may be applied to the entire IOL or to only a portion of the IOL. As used herein, "implants" includes contact lenses.

In order to prepare the implant material to be coated so that it is capable of receiving the coating, it may be necessary or desirable to expose the surface to be coated to a reactive plasma gas prior to applying the coating composition of the present invention. Suitable reactive plasma gases include oxidizing gases, such as oxygen gas. A suitable plasma chamber is the P$^2$CIM B-Series plasma chamber made by Advanced Plasma Systems, Inc. Using such a chamber, suitable plasma parameters include: power=400 W, plasma gas=oxygen; pressure of the plasma gas=225 mTorr; exposure time=4–6 minutes.

The following examples are intended to be illustrative but not limiting.

EXAMPLES 1–4

The formulations shown in Table 1 below were prepared and cured in polypropylene slab molds (10 mm×20 mm×0.9 mm). The formulations of Examples 1–3 were cured by exposure to blue light for one hour using a Kulzer Palatray CU blue light unit (12–14 mW/cm$^2$). The formulation of Example 4 was cured by heating for one hour at 75° C., followed by one hour at 100° C.

Copolymer Purification

Next, the cured copolymers were extracted to remove any aqueous and non-aqueous leachables. After the formulations of Examples 1–4 were cured, they were extracted in de-ionized water overnight, followed by oven drying at 110–120° C. for two hours. If the copolymer is not adequately dried, it will form a gel in hydrophobic solvents. The dried formulations were then dissolved in dichloromethane to make approximately 10% (pbw) solutions, and the solutions added to 100 cc of toluene. The resulting solutions were then transferred to a 500-cc flask and the dichloromethane stripped off using a rotovap at about 60° C. Following stripping, sufficient toluene was added to the solutions to bring each to a total weight of about 100 g. The solutions were then cooled to room temperature. After reaching room temperature, each solution was quickly added to 400-cc of hexane with stirring to precipitate the desired copolymer, leaving any low molecular weight, non-hydrophilic extractables in solution. The solvent was decanted and the copolymer precipitate (powder) soaked for several hours in 300 cc of fresh hexane (purity 99+%). The hexane was again decanted and the copolymers placed under high vacuum (<0.2 mm Hg) at room temperature for two hours to give the desired purified copolymers.

Coating Solution Preparation

The purified copolymers were each dissolved in 50:50 (pbw) ethanol:2-pentanone solvent to give the desired concentration (typically 4–5%). The copolymer of Example #1 was prepared as a 4.2% solution. The copolymers of Examples 2–4were prepared as 4.6%, 4.0% and 4.0% solutions, respectively. The resulting solutions were filtered through a Gelman glass fiber Acrodisc (1 $\mu$m) to give particulate-free coating solutions.

Coating Application

A copolymer comprising 65% 2-phenylethyl acrylate; 30% 2-phenylethyl methacrylate; 1.8% o-methallyl Tinuvin P; and 3.2% 1,4-butanediol diacrylate was prepared using 1.8% Perkadox-16 as a thermal initiator. This copolymer was cured in the slab molds described above, extracted in acetone for approximately 2 hours, dried in air at room temperature for about 1 hour, and then dried in an oven at 100° C. for about 1 hour. This material in the form of the defined slabs served as the implant/substrate material for all Examples ("the implant slabs").

The implant slabs were dipped in the coating solutions. Caution is taken to minimize the immersion time of the samples in the coating solution as the solvent will swell the sample. The coated implant was allowed to dry in air at room temperature for 15 minutes, followed by baking at 70° C. for 30 minutes. The coating copolymer was not imbibed into the implant slab's surface, and did not react (i.e. via covalent bonds) with the substrate. The coating can be easily removed by a variety of organic solvents or solvent mixtures, including the same solvent base as was used to prepare the coating solution.

In order to demonstrate that the coatings did not dissolve in water, the coated samples from Examples 2–4 were stored in de-ionized water for three months and then exposed to a 0.05% aqueous solution of Congo Red dye, which complexes with vinyl pyrrolidone. All samples were stained red. The coating was not removed by mild wiping or rubbing with moist fingers.

TABLE 1

(all amounts in parts by weight, except as noted)

| INGREDIENT | 1 | 2 | 3 | 4 |
|---|---|---|---|---|
| 2-PEMA | 29.32 | 39.69 | 39.99 | — |
| 2-PEA* | — | — | — | 29.80 |
| NVP | 54.64 | 44.54 | 44.15 | 69.16 |
| PEG (400) Monomethylether Monomethacrylate | 14.84 | 14.72 | 14.84 | — |
| 1-Dodecanethiol | — | — | 0.06 | 0.07 |
| Lucirin TPO** | 1.18 | 1.05 | 0.96 | — |
| t-Butylperoctoate | — | — | — | 0.96 |
| % water | 88.7 | 65.9 | 72.2 | 73.5 |
| Refractive Index | 1.360 | 1.398 | 1.386 | 1.38 |

*2-Phenylethoxylacrylate
**2,4,6-trimethyl-benzoyl diphenylphosphine oxide

EXAMPLES 5–7

Coated implant slabs were prepared according to the procedure described above for Examples 1–4, except that the coating copolymer contained the ingredients shown in Table 2 below. The formulations of Examples 5 and 6 were cured using the Kulzer Palatray CU unit for one hour. The formulation of Example 7 was cured using the same unit for 0.75 hr. In all three cases, the coating solution was prepared as a 4–5% solution of the copolymer in a 50:50 (pbw) ethanol:2-pentanone solvent, filtered through a Gelman glass fiber Acrodisc and applied to implant slabs by dip-coating. The coated implant slabs were dried in air at room temperature for 15 minutes, followed by baking at 70° C. for 30 minutes.

These examples show that copolymers of NVP with methyl methacrylate or 4-phenylbutyl methacrylate gave significantly worse haze upon hydration than with 2-PEMA. Example 6 gave only 9.1% aqueous extractables and produced only a slight haze when hydrated. In contrast, Examples 5 and 7 were opaque when hydrated. Example 5 crazed badly and began to disintegrate when heated at 55° C. in de-ionized water. Example 7 gave 20.6% aqueous extractables.

TABLE 2

(all amounts in parts by weight)

| INGREDIENT | 5 | 6 | 7 |
|---|---|---|---|
| 4-Phenylbutylmethacrylate | 1.5038 | — | — |
| 2-PEMA | — | 1.2519 | — |
| Methyl methacrylate | — | — | 1.2688 |
| NVP | 3.4992 | 3.5067 | 3.4979 |
| Lucirin TPO | 0.0537 | 0.0553 | 0.0484 |
| % Water | N/A | 73.5 | 92.3 |

EXAMPLE 8

Coated implant slabs were prepared according to the procedure described above for Examples 1–4, except that the coating copolymer contained the ingredients shown in Table 3 below. As in the case of Examples 1–4 above, the coating was cured using the Kulzer Palatray CU unit for one hour. The coating solution was prepared as a 5.7% solution of the coating copolymer in a 50:50 (pbw) ethanol:2-pentanone solvent. After the implant slabs were dipped in the coating, the coated implant slabs were allowed to air dry at room temperature followed by baking for 20 minutes at 80° C. The coated slabs were then stored in de-ionized water at room temperature overnight. The coated slabs were then gently wiped or rubbed with wet fingers and then subjected to a fog (i.e., breath) test. The slab is held near the mouth while exhaling. If the coating is present, little if any condensation will appear on the slab. If the coating is no longer present, however, the surface will fog. In this case, the tested slabs fogged, indicating that the coating had been removed when gently wiped or rubbed with wet fingers.

TABLE 3

(all amounts in parts be weight)

| Ingredient | 8 |
|---|---|
| 2-PEMA | 39.57 |
| GMMA | 29.52 |
| PEG (400) Monomethylether Methacrylate | 29.66 |
| 1-Dodecanethiol | 0.40 |
| Lucirin TPO | 0.84 |
| % Water (slab) | 71.5 |
| Refractive Index (hydrated) | 1.388 |

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

I claim:

1. A copolymeric coating composition for a surgical implant wherein the coating composition comprises a non-covalently cross-linked copolymer of 2-phenylethyl (meth) acrylate and N-vinyl pyrrolidone, and the coating composition is capable of absorbing from about 40 to about 90% water.

2. The coating composition of claim 1 wherein the 2-phenylethyl(meth)acrylate is 2-phenylethyl methacrylate.

3. The coating composition of claim 1 wherein the coating composition is capable of absorbing from about 65 to about 75% water.

4. The coating composition of claim 1 wherein the copolymer comprises from about 25 to about 60% of 2-phenylethyl (meth)acrylate and about 40 to about 75% of N-vinyl pyrrolidone.

5. The coating composition of claim 4 wherein the copolymer comprises from about 35 to about 45% of 2-phenylethyl (meth)acrylate and about 40 to about 50% of N-vinyl pyrrolidone.

6. The coating composition of claim 1 wherein the coating composition further comprises one or more ingredients selected from the group consisting of UV absorbers that are copolymerizable with the 2-phenylethyl (meth)acrylate and NVP ingredients; blue-light blocking colorants that are copolymerizable with the 2-phenylethyl (meth)acrylate and NVP ingredients; reactive plasticizers; and chain transfer agents.

7. The coating composition of claim 6 wherein the coating composition comprises a reactive plasticizer selected from the group consisting of polyethylene glycol (200–2000) mono(meth)acrylates and polyethylene glycol (200–2000) monomethylether mono(meth)acrylates.

8. The coating composition of claim 7 wherein the reactive plasticizer is polyethylene glycol (400) monomethylether monomethacrylate.

9. The coating composition of claim 6 wherein the coating composition comprises a chain transfer agent selected from the group consisting of 1-dodecanethiol and 2-mercaptoethanol.

* * * * *